United States Patent [19]

Percarpio

[11] 4,317,456

[45] Mar. 2, 1982

[54] MULTIPLE SAMPLE NEEDLE WITH ANTI-BACKFLOW VALVE

[75] Inventor: Edward P. Percarpio, North Haledon, N.J.

[73] Assignee: Becton, Dickinson and Company, Paramus, N.J.

[21] Appl. No.: 129,149

[22] Filed: Mar. 10, 1980

[51] Int. Cl.³ ............................................. A61B 5/14
[52] U.S. Cl. .................................................. 128/766
[58] Field of Search ............... 128/764, 766, 218 NV, 128/274, 276; 137/843; 251/4, 7

[56] References Cited

U.S. PATENT DOCUMENTS

| | | | |
|---|---|---|---|
| 3,498,321 | 3/1970 | Barrett et al. | 137/843 |
| 3,557,778 | 1/1971 | Hughes | 128/764 X |
| 3,807,445 | 4/1974 | McPhee | 137/843 X |
| 3,889,710 | 6/1975 | Brost | 137/843 X |
| 3,970,106 | 7/1976 | Harris | 137/843 |
| 4,207,870 | 6/1980 | Eldridge | 128/218 NV |
| 4,244,378 | 1/1981 | Brignola | 137/843 X |

Primary Examiner—John D. Yasko
Attorney, Agent, or Firm—Richard J. Rodrick

[57] ABSTRACT

A valved multiple sample needle assembly for use with a vacuum collection device in obtaining fluid samples, particularly from a patient. The assembly comprises a housing with a chamber therein and having first and second access openings in fluid communication with the chamber. A valve seat associated with the first access opening faces the chamber, while a needle cannula extends outwardly from the first access opening. A resilient, collapsible valve member is positioned in the chamber and normally contacts the valve seat to serve as a closed valve. This valve member is adapted to resiliently collapse and operatively break the sealing engagement with the valve seat when the pressure at the second access opening is sufficiently negative with respect to the pressure at the first access opening so that fluid can flow into the chamber and then out of the second access opening. Backflow is prevented into the first access opening, since the valve member will close should fluid flow in that direction.

18 Claims, 7 Drawing Figures

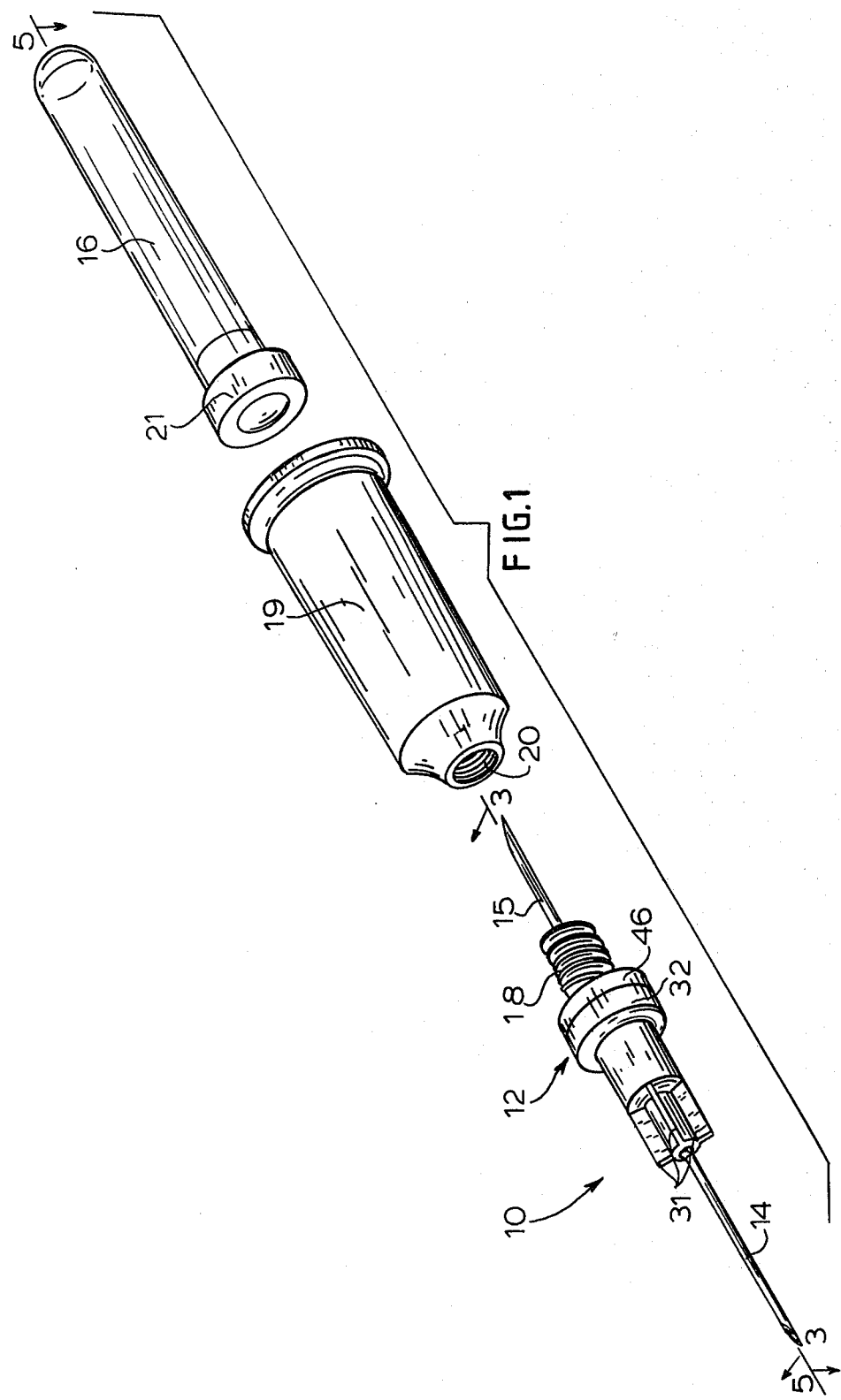

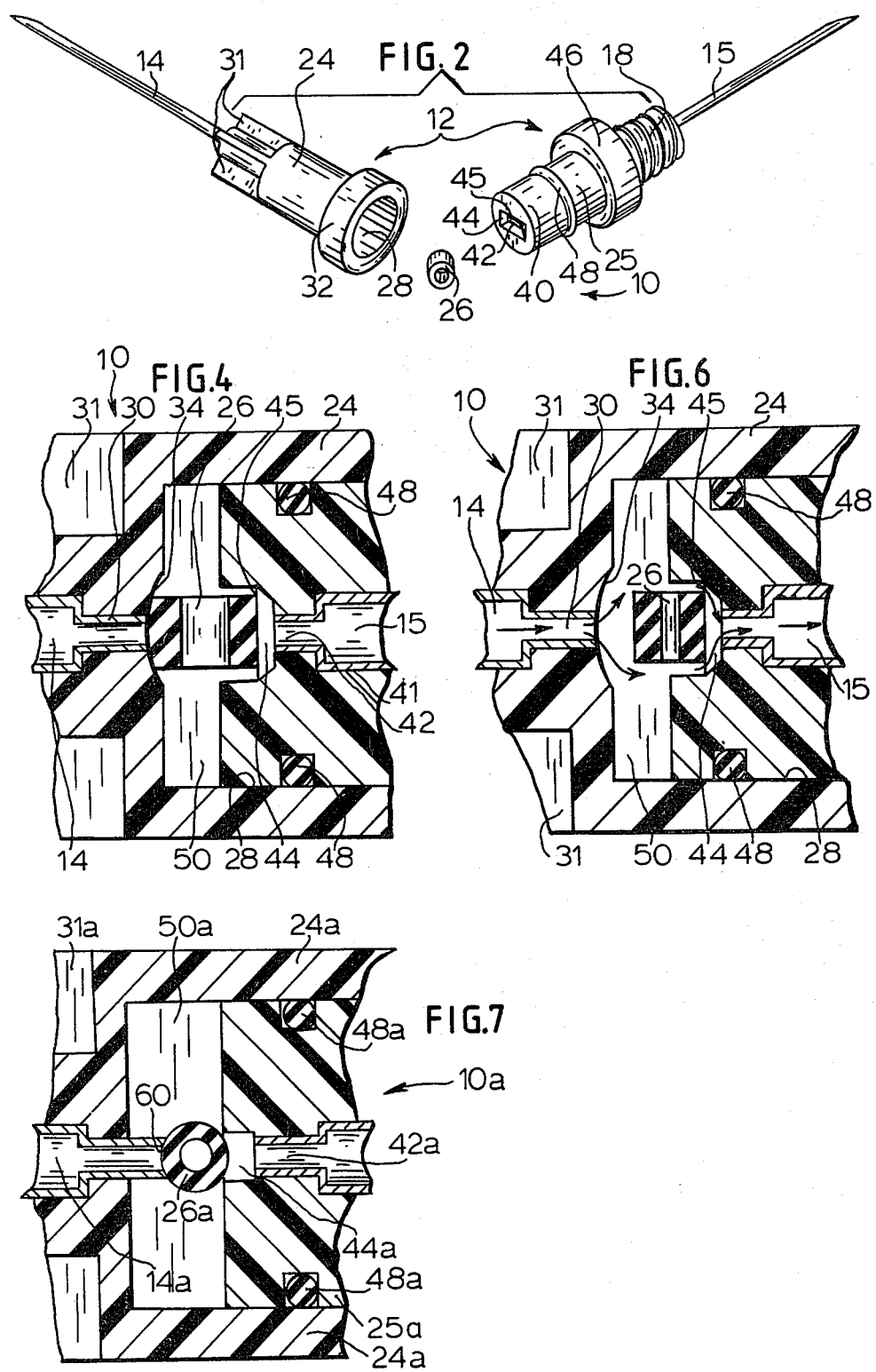

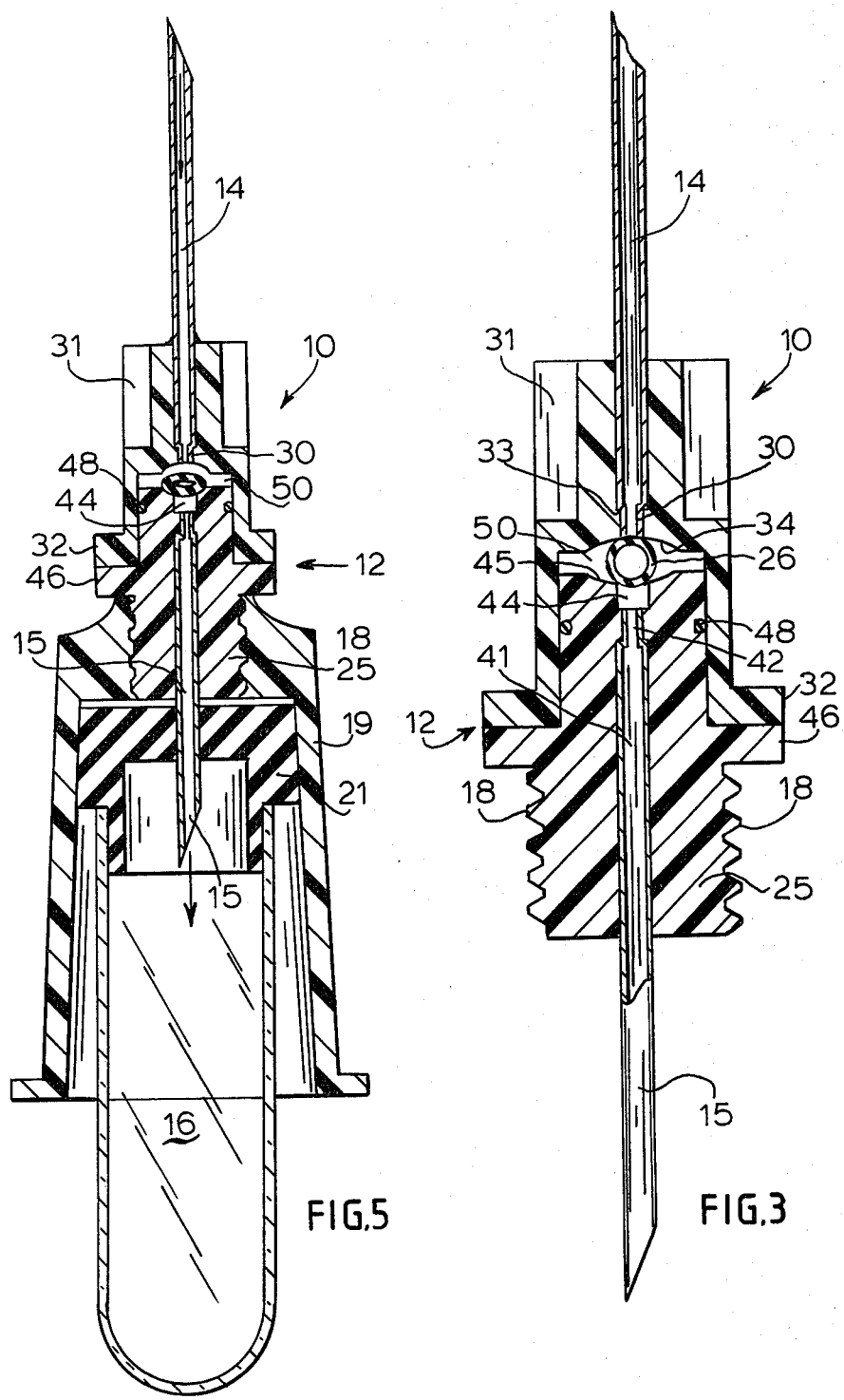

MULTIPLE SAMPLE NEEDLE WITH ANTI-BACKFLOW VALVE

BACKGROUND OF THE INVENTION

The present invention relates to a needle assembly for collecting fluid such as from a patient, and more particularly, concerns a needle assembly for collecting multiple samples of fluid from a patient with an anti-backflow valve included in the assembly.

In the collection of fluids, and especially when such fluids may be blood or other bodily fluids from a patient, it is most desirable that backflow into the patient or other source be prevented. The reasons for prevention of fluid back into the patient are numerous. For example, when collecting blood into a collection container, various chemicals or other reagents may be present in the container for different tests on the blood sample. As the blood sample flows into this container, it mixes with the chemical therein. Should this mixture backflow into the patient, the chemical would then enter the patient's blood stream with potential harm to the patient. Another instance where backflow into the patient could be problematical involves clotting of the blood during the collection procedure. Should a small amount of the collected blood clot somewhere in the collection needle or container, backflow of such a clotted or coagulated amount of blood into the patient could cause serious difficulties. Accordingly, the inclusion of some type of anti-backflow device or valve into a needle assembly for the collection of fluids from a patient is a desired feature.

Attempts have been made previously to include such an anti-backflow valve in needle assemblies. These valves have been proposed in various shapes and forms, notably including shiftable ball valves, cup valves, disk valves with a self-sealing slit therein, and "duck bill" valves which open and close under differential fluid pressures. While, for instance, the ball valve is simple and straightforward to manufacture, there are problems inherent in the use of such a ball as a one-way valve. In particular, the mass of the ball generally takes a substantially large fluid differential in order to cause movement to open and close the valve. This is a shortcoming, especially when the pressures involved in the collection of the fluid sample may not be great. A ball valve for incorporation in a needle assembly is illustrated in U.S. Pat. No. 3,557,778. Some of the other aforementioned one-way valves suffer from a variety of deficiencies, both in structure and function. For instance, unless the one-way valve is reproducible from one valve to the next, it is difficult to predict accurately the pressures under which it will function. Thus, the inclusion of this type of valve in the needle assembly could produce unpredictable results. Moreover, some of the aforementioned valves are difficult to manufacture with concomitantly higher expense involved in their production and assembly into the needle structure. Accordingly, it can be seen that there is still room for improvement in anti-backflow valves which are used in multiple sample needle assemblies, particularly useful in obtaining blood samples from a patient.

SUMMARY OF THE INVENTION

A valved multiple sample needle assembly for use with a vacuum collection device in obtaining fluid samples from a patient comprises a housing with a chamber therein and having first and second access means therethrough in fluid communication with the chamber. Valve seat means is associated with the first access means facing the chamber, with a cannula for insertion into a patient extending from the first access means in fluid communication with the chamber. Resilient, collapsible valve means is positioned in the chamber and normally contacts the valve seat means in fluid sealing engagement therewith to serve as a closed valve when the pressure at the second access means is substantially equal to or positive with respect to the first access means. The valve means is adapted to resiliently collapse and operatively break the sealing engagement with the valve seat means when the pressure at the second access means is sufficiently negative with respect to the pressure at the first access means to serve as an open valve thereby allowing fluid to flow from the first access means into the chamber and out of the second access means.

In a preferred embodiment of the needle assembly of the present invention as basically described above, the housing has a forward end, a rearward end with the chamber within. A first cannula extends from the first access opening and is adapted for insertion into a patient. The interior opening of this cannula may extend a short distance into the chamber to provide a valve seat. Extending from the second access opening in the rearward end of the housing is a second cannula which is adapted for penetration of an evacuated container for collection of a blood sample. The valve means is preferably a hollow, cylindrically shaped, resilient, collapsible tube positioned in the chamber with its longitudinal axis lying substantially perpendicular to the longitudinal axis of the first cannula. A portion of the peripheral surface of the valve tube is adapted to contact the valve seat for sealing engagement therewith. Furthermore, the valve tube is constrained in the chamber to prevent its movement other than collapse in the direction parallel to the longitudinal axis of the first cannula.

In another embodiment of the present invention, the assembly includes a holder for an evacuated container connected to the housing.

In accordance with the principles of the present invention, there are structural elements and features herein which are notably different from prior anti-backflow valves for use in needle assemblies in a number of respects. For instance, the present valved multiple sample needle assembly includes an anti-backflow valve which operates by virtue of its resilient collapsibility under differential pressures. In this fashion, the valve seat can be a very small opening through the housing or even the interior open end of the needle cannula which extends into the chamber. The valve of the present invention is situated in a chamber, the walls of which can be dimensionally controlled, along with the properties of the valve member itself, to predictably regulate the pressure for the opening and closing of the valve. In addition, the valve of the present invention is readily reproducible so that there will be little variation in the valve in different needle assemblies of this type. Furthermore, the expense involved in manufacturing the valve of the present invention is low when compared with the expense involved in fabricating the more sophisticated type of anti-backflow valves which have been attempted previously. Assembly of the valve into the needle assembly is also straightforward and requires a minimal amount of fabrication steps during the assembly procedure. As a result of the foregoing, the anti-backflow valve in the multiple sample needle assembly of the present invention provides significant advantages over previously proposed valves intended for similar use.

BRIEF DESCRIPTION OF THE DRAWINGS

FIG. 1 is an exploded perspective view illustrating the preferred valved multiple sample needle assembly, a holder for an evacuated container and an evacuated blood collection container for use in obtaining blood samples from a patient;

FIG. 2 is an exploded perspective view illustrating the components of the preferred valved multiple sample needle assembly of the present invention;

FIG. 3 is an enlarged cross-sectional view taken along line 3—3 of FIG. 1;

FIG. 4 is an enlarged sectional view of the chamber area of the housing;

FIG. 5 is a cross-sectional view taken along line 5—5 of FIG. 1 with the components in an assembled condition as they would appear during use;

FIG. 6 is an enlarged sectional view of the chamber area of the housing illustrating the function of the valve member during use; and FIG. 7 is a partial sectional view similar to the view of FIG. 3 illustrating an alternate embodiment of the valve member and valve seat cooperative arrangement.

DETAILED DESCRIPTION

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims.

Adverting to the drawings, particularly to FIG. 1, there is illustrated the preferred embodiment of a valved multiple sample needle assembly 10. The basic external components of needle assembly 10 include a housing 12, a first needle cannula 14 adapted for insertion into a patient and a second needle cannula 15 at the opposite end of housing 12, the second needle cannula adapted for penetration of an evacuated container 16 for collection of a blood sample. Housing 12 includes a threaded portion 18 adjacent second cannula 15 onto which a container holder 19 is threaded by its internal mating threads 20 at the forward end of the holder. Evacuated container 16 slides into holder 19 so that second needle cannula 15 can penetrate the prenetrable stopper 21 at the forward end of the evacuated container. These general aspects of multiple sample blood collections in this type of structure are well known to those skilled in this art.

In FIGS. 2, 3 and 4, the detailed construction of needle assembly 10 is illustrated. Housing 12 has a forward end 24 and a rearward end 25, these ends being separable in order to place valve member 26 in its proper position. Forward end 24 is preferably cylindrically shaped and has a large bore 28 extending into and partially through its body. At the other end of this section, a smaller bore 29 is included which is generally sized to slidably fit needle cannula 14 therein. In this embodiment being described, smaller bore 29 does not extend completely through forward end 24 to communicate with larger bore 28. However, a still smaller diameter channel 30 interconnects these two bores so that there is fluid communication from needle cannula 14 into larger bore 28. At the junction between bore 29 and channel 30 a shoulder 33 is formed. Needle cannula 14 abuts against this shoulder 33 for proper positioning. Once the needle cannula is in position it can be suitably affixed such as by adhesive means or the like. It is appreciated that the presence of channel 30 is not essential to the structure of this forward end of the housing, but is merely a preferable element. However, it will be appreciated that the diameter of channel 30 can be varied to provide a regulation of the fluid flow rate which flows therethrough. This fluid flow regulation will, in turn, provide a control of the pressure force to open valve member 26, as hereinafter discussed, inasmuch as the force to open the valve is related to the diameter of the opening through which the fluid exits.

Forward end 24 of the housing also includes a number of longitudinal ribs 31 surrounding the outwardly extending cannula. A needle shield (not shown) generally covers the outwardly extending needle cannula and includes mating internal ribs within. The mating ribs between needle shield and needle assembly allow the user to facilitate the insertion or removal of the needle assembly into the tube holder. Forward end 24 also includes an annular flange 32 which serves to provide a surface for joining the two portions of the housing together upon assembly. Once again, suitable fastening means, such as adhesives or the like may be used to secure the two portions of the housing together.

On the interior wall of large bore 28 through which channel 30 emerges, an arcuate shaped recess 34 is preferably included. Recess 34 generally has a larger radius than the radius of valve member 26, but this rounded surface provides a conformity to the surface of the valve member at the point of contact engagement. Inasmuch as recess 34 and the opening of channel 30 serve as the valve seat for valve member 26, the slightly rounded surface contributes to the effectiveness of the sealing engagement at this point. It is noted particularly when referring to FIG. 4, that recess 34 does not extend all the way across the interior wall of bore 28. While it is wider in width than the longest transverse length of valve member 26, it cannot be too wide so that the valve member would slide laterally away from the opening of channel 30, thereby rendering the valve seat engagement useless.

Rearward end 25 includes a protruding portion 40, generally cylindrically shaped, and sized to fit within larger bore 28 of the forward end. At the opposite side of this rearward end, external threads 18 are provided as previously mentioned for providing a connection mechanism to the tube holder. A bore 41 extends partially through the rearward end of the housing which is substantially similar to bore 29 in the forward end of the housing. Once again, bore 41 is sized to accept the diameter of second needle cannula 15, which is secured to bore 41 by appropriate means, including adhesives and the like. A smaller diameter channel 42 communicates with bore 41 on one end, and communicates with a transverse groove 44 on its other end. Fluid is thus allowed to communicate between needle cannula 15 and groove 44 which provides an opening for the entrance of fluid in this portion of the housing. An arcuately shaped recess 45 is formed into the end wall of this section of the housing just over groove 44. An annular flange 46 is provided to cooperate with flange 32 in joining the two ends of the housing together. To assure proper fluid flow through the housing, an annular, elastomeric ring 48 is included around protruding portion 40. Upon assembling forward end and rearward end together, with valve member 26 placed in its proper position, respective flanges 32 and 46 are secured together by appropriate fastening means, such as adhesives and the like. Protruding portion 40 within larger bore 28 leaves an internal space around valve member 26 forming a chamber 50 within the housing. The wall with arcuate recess 34 therein forms a forward wall of the chamber, while the wall with arcuate recess 45 therein forms a rearward wall of the chamber.

Valve member 26 is preferably a short section of hollow, cylindrical tubing, being resilient and collapsible in nature, with its inside diameter and outside diameter preferably substantially concentric to each other, and both ends preferably being open. This structure provides more control and uniformity during the functioning of the valve in use. During assembly, valve member 26 is positioned in chamber 50 so that its longitudinal axis lies transversely, and preferably perpendicularly, with respect to the longitudinal axis of cannula 14. Under static conditions, i.e., when the fluid pressures on both sides of valve member 26 are substantially equal, a portion of the peripheral surface of the valve member is adapted to contact opening 30. This contact is assured by controlling the physical dimensions such as the length of chamber, depth of the respective recesses on opposite walls of the chamber and the diameter of the valve member itself. A slight compression of the valve member within the chamber during assembly will suit this purpose. It is noted, by referring particularly to FIG. 4, that groove 44 is longer in its transverse dimension than the greatest transverse length of valve member 26. This will assure that fluid will be able to flow from chamber into some portion of groove 44, then through channel 42 into second cannula 15 for ultimate deposit within the evacuated blood collection container. This structural configuration thereby provides a constraint of the valve member within the chamber. In particular, since flow of fluid is expected to flow from first cannula 14 through the housing and into second cannula 15, the rearward wall, and specifically recess 45, prevent movement of valve member 26 other than compressibility or collapse in the direction parallel to the longitudinal axis of cannula 14. There may be some lateral or transverse movement of valve member 26 within chamber 50 depending upon the respective widths of recesses 34 and 45. Accordingly, FIGS. 3 and 4 depict the valve member as it appears in the closed position which occurs when the pressures at the openings on opposite sides of the valve member are substantially equal or if the pressure at groove 44 is positive with respect to the pressure at channel 30. This just mentioned positive pressure would occur, for example, if for some reason the venous pressure of the patient drops below the pressure at second cannula 15. If this happens, fluid in the needle assembly would tend to backflow into the patient. However, this positive pressure at groove 44 will induce valve member 26 to close against channel opening 30.

Turning now to FIGS. 5 and 6, the operation of valved multiple sample needle assembly 10 is illustrated in conjunction with an attached tube holder 19 and evacuated blood collection container 16 in position. Collection container 16 is slid into holder 19 so that penetrable stopper 21 is penetrated by hollow cannula 15. It is noted, for ease of use and convenience that needle cannula 15 which penetrates into the evacuated container is in substantial axial alignment with first needle cannula 14 on the opposite side of the needle assembly housing. Once second cannula 15 is into the vacuum area inside container 16, the pressure at groove 44, in fluid communication now with the vacuum inside container 16, becomes negative with respect to the pressure at channel opening 30 on the opposite side of valve member 26. Allowing for any residual resistive compressive forces in the valve member material, this negative pressure causes valve member 26 to resiliently collapse and operatively move away from and break its sealing engagement at channel opening 30. At this time, needle cannula 14 has already been inserted into the vein of the patient so that blood may now flow through cannula 14 and into chamber 50 since valve member 26 is now open. Blood continues to flow into groove 44, channel 42 and on through cannula 15 for ultimate collection into container 16. As seen more clearly in FIG. 6, the arrows indicate the direction of blood flow through needle assembly 10. It is noted that the wider transverse dimension of groove 44 allows the blood to flow around valve member 26 for proper flow through the needle assembly. In the open condition, valve member 26 is collapsed to a more flat condition than when the valve member is closed against the valve seat. If backflow of any blood or other fluids should occur, valve member 26 is adapted to resiliently spring back against the valve seat represented by channel opening 30 to thereby close off fluid flow. When the user of this composite assembly has collected enough blood into container 16, the filled container is withdrawn thereby terminating the vacuum conditions at cannula 15. Valve member 26, perceiving this change of pressure, springs back to close off channel opening 30. It should be pointed out that the spring force of the collapsible valve member should be sufficient to provide a closed valve even while needle cannula 14 remains inserted into the vein of the patient. This compressive spring force in valve member 26 must then be higher than the maximum venous pressure expected to be encountered in the normal use of this type of blood collection combination.

Other variations and embodiments of the present invention are contemplated and fall within the purview of this invention. One such other embodiment is illustrated in FIG. 7 and basically includes a modification in the position of the needle cannula at the forward end of the housing. In this embodiment, needle cannula 14a is inserted through a bore 29a which extends completely through forward end 24a. Cannula 14a is secured within bore 29a, by appropriate fastening means, so that the interior opening 60 of the hollow cannula extends a short distance into chamber 50a to provide a valve seat for engagement by valve member 26a. As in the previously described embodiment, this valve seat at opening 60 may include an arcuately shaped recess therein to provide better conformity to the peripheral surface of valve member 26a at the point of contact.

The valve member of the present invention is preferably made of elastomeric material sufficiently soft to collapse under the influence of a low level pressure differential on opposite sides of the valve member. In situations where blood is being collected from a patient, the pressure differential to collapse the valve member and move the contacting portion away from sealing engagement is in the range of thirty (30) millimeters of mercury to seventy (70) millimeters of mercury. As a choice of elastomeric material, the valve member is preferably made from silicone rubber. In a typical needle assembly, one version of the preferred valve member as described above, has an inside diameter of 0.133 inches (0.338 centimeters), and wall thickness of 0.02 inches (0.051 centimeters) and is 0.125 inches (0.318 centimeters) long. The durometer of this tubing is approximately 50–70 Shore A.

Thus, the valved multiple sample needle assembly of the present invention includes an anti-backflow valve which is easily mounted in the assembly, inexpensive to produce and functional in its operation. In addition, the valve member of this invention allows the opening and closing pressures of the valve to be predicted straightforwardly based on a simple pressure seal arrangement. Moreover, the valve member includes a consistency which makes it repeatable from assembly to assembly for better control over its use.

What is claimed is:

1. A valved multiple sample needle assembly for use with an evacuated container in obtaining blood samples from a patient comprising:
    a housing having a forward end, a rearward end and a chamber within;
    a first access opening through the forward end of said housing in fluid communication with said chamber;
    a cannula extending outwardly from said first access opening in fluid communication with said chamber and being adapted for insertion into a patient;
    a second access opening through the rearward end of said housing in fluid communication with said chamber; and
    a resilient, collapsible valve member positioned in said chamber and normally contacting said first access opening in a fluid-sealing arrangement therewith when the pressure at said second opening is substantially equal to or positive with respect to the first access opening to serve as a closed valve, said valve member adapted to resiliently collapse and operatively move away from said sealing engagement with said first access opening when the pressure at said second opening is sufficiently negative with respect to the pressure at said first opening to serve as an open valve thereby allowing fluid to flow from said first access opening into said chamber and out of said second access opening, said chamber including a rearward wall having a transverse groove therein communicating with said second opening, said groove being longer than the greatest transverse length of said valve member so that fluid can flow into said groove when said valve member is collapsed, said valve member being positioned in said groove in both the open and closed positions thereof and adapted to be constrained therein.

2. The assembly of claim 1 wherein said valve member is collapsed to a more flat condition when said valve is open than when said valve is closed.

3. The assembly of claim 1 wherein said valve member is cylindrically shaped with its longitudinal axis lying transversely with respect to the longitudinal axis of the cannula and with a portion of its peripheral surface adapted to contact said first access opening for said sealing engagment.

4. The assembly of claim 3 wherein said cylindrically shaped valve member is hollow.

5. The assembly of claim 4 wherein said hollow valve member is a hollow tube having both ends open.

6. The assembly of claim 5 wherein said hollow tube has an inside diameter and an outside diameter in substantial concentricity with each other.

7. The assembly of claim 1 wherein said valve member is made of elastomeric material sufficiently soft to collapse under the influence of a low level pressure differential on opposite sides of said valve member.

8. The assembly of claim 7 wherein the pressure differential to collapse said valve member and move the contacting portion away from said sealing engagement is in the range of 30 to 70 millimeters of mercury.

9. The assembly of claim 7 wherein the elastomeric material is silicone rubber.

10. The assembly of claim 1 wherein said first and said second openings are in substantial alignment on opposite sides of said chamber with said cannula extending outwardly in a direction substantially parallel to said alignment axis.

11. The assembly of claim 1 wherein a second cannula extends from said second access opening in fluid communication with said chamber and being adapted for penetration of an evacuated container for collection of a blood sample.

12. The assembly of claim 1 wherein the housing includes means for connecting a holder for an evacuated container.

13. The assembly of claim 12 which further includes a holder for an evacuated container connected to said housing.

14. The assembly of claim 1 wherein the first access opening is shaped to conform to the surface of said valve member at the point of contact engagement with said valve member.

15. The assembly of claim 1 wherein the interior end of said first access opening has a different diameter from the remaining part of said access opening in order to provide selective control over the fluid force through the same against the valve member.

16. The assembly of claim 1 wherein the interior opening of the cannula extends a short distance into said chamber to provide a valve seat for engagement by said valve member.

17. A valved multiple sample needle assembly for use with a vacuum collection device in obtaining fluid samples from a source of fluid comprising:
    a housing with a chamber therein and having first and second access means therethrough in fluid communication with said chamber;
    valve seat means associated with the first access means facing said chamber;
    a cannula for insertion into said fluid source extending from said first access means in fluid communication with said chamber;
    said second access means adapted for fluid communication with said vacuum collection device; and
    resilient, collapsible valve means positioned in said chamber and normally contacting said valve seat means in fluid-sealing engagement therewith to serve as a closed valve when the pressure at said second access means is substantially equal to or positive with respect to the first access means, said valve means adapted to resiliently collapse and operatively break said sealing engagement with said valve seat means when the pressure at said second access means is sufficiently negative with respect to the pressure at said first access means to serve as an open valve thereby allowing fluid to flow from said first access means into said chamber and out of said second access means, said chamber including a rearward wall having a transverse groove therein communicating with said second access means, said groove being longer than the greatest transverse length of said valve means so that fluid can flow into said groove when said valve means is collapsed, said valve means being positioned in said groove in both the open and closed positions thereof and adapted to be constrained therein.

18. A valved multiple sample needle assembly for use with an evacuated container in obtaining blood samples from a patient comprising:

a housing having a forward end, a rearward end and a chamber within;

a first access opening through the forward end of said housing in fluid communication with said chamber;

a first cannula extending from said first access opening in fluid communication with said chamber and being adapted for insertion into a patient, the interior end of said first access opening serving as a valve seat;

a second access opening through the rearward end of said housing in fluid communication with said chamber, said first and second openings being in substantial alignment on opposite sides of said chamber;

a second cannula extending from said second access opening in fluid communication with said chamber and being adapted for penetration of an evacuated container for collection of a blood sample; and a hollow, cylindrically shaped resilient, collapsible valve member positioned in said chamber with its longitudinal axis lying substantially perpendicular to the longitudinal axis of said first cannula and with a portion of its peripheral surface adapted to contact said valve seat for sealing engagement therewith, said valve seat being shaped to conform to the surface of said valve member at the point of contact engagement with said valve member to facilitate said sealing engagement, said valve member being constrained in a transverse groove in a rearward wall of said chamber to prevent movement other than collapse in the direction parallel to the longitudinal axis of said first cannula, said valve member normally contacting said valve seat in a fluid-sealing engagement therewith when the pressure at the second opening is substantially equal to or positive with respect to the valve seat to serve as a closed valve, said valve member adapted to resiliently collapse and operatively move away from said sealing engagement with said valve seat when the pressure at said second opening is sufficiently negative with respect to the pressure at the valve seat to serve as an open valve thereby allowing fluid to flow from said first cannula into said chamber and out of said second cannula.

* * * * *